United States Patent [19]

Sun

[11] Patent Number: 4,834,077

[45] Date of Patent: May 30, 1989

[54] STERILE DISPOSABLE LINGUIFORM LARYNGOSCOPE BLADE SHEATH

[76] Inventor: William Y. Sun, 401 N. Armistead St., Apt. 104, Alexandria, Va. 22312-2845

[21] Appl. No.: 917,691

[22] Filed: Sep. 16, 1986

Related U.S. Application Data

[63] Continuation-in-part of Ser. No. 713,694, Mar. 19, 1985, abandoned.

[51] Int. Cl.⁴ .................................................. A61B 1/06
[52] U.S. Cl. .......................................... 128/11; 128/16
[58] Field of Search ........................... 128/11, 15, 16, 3

[56] References Cited

U.S. PATENT DOCUMENTS

| | | | |
|---|---|---|---|
| 3,426,749 | 2/1969 | Jephcott | 128/11 |
| 3,851,642 | 12/1974 | McDonald | 128/18 |
| 3,856,001 | 12/1974 | Phillips | 128/11 |
| 4,344,419 | 8/1982 | Burgin | 128/3 |
| 4,425,909 | 1/1984 | Rieser | 128/11 |

FOREIGN PATENT DOCUMENTS 2381528 10/1978 France .................... 128/11

OTHER PUBLICATIONS

Grandilli, Peter; *Technician's Handbood of Plastics;* 1981; (pp. 207, 209, 2210).

Primary Examiner—Richard C. Pinkham
Assistant Examiner—Mark S. Graham

[57] ABSTRACT

This disclosure is directed to an improved laryngoscope blade sheath for use in the intubation process to maximize laryngoscope use by providing a single unit to orchestrate the laryngescope and the endotracheal tube. This invention is a sterile, disposable, generally linguiform laryngoscope blade sheath. The sheath is made mostly from a fairly rigid material. The inside of the sheath is hollow so that all the common standard laryngoscope blades can be inserted through its aperture. The width of the sheath is wider than the common blades and the shape of the sheath is curved and spoon-like so that the tongue can be lifted stably without slipping. There are orifices on the underneath surface of the sheath so that the light of the laryngoscope blade can shine through these orifices and the trachea can be visualized. The sheath also has an intubation guide groove underneath to make intubation more efficent. Because this sheath is used only once there is no danger of cross infection.

11 Claims, 2 Drawing Sheets

STERILE DISPOSABLE LINGUIFORM LARYNGOSCOPE BLADE SHEATH

CROSS REFERENCE

This application is a continuation-in-part of Ser. No. 06/713, 694, filed Mar. 3, 1985 and now abandoned.

BACKGROUND OF THE INVENTION

1. FIELD OF THE INVENTION

In many emergency situations in order to save lives or give anesthetics for surgery in operation rooms, physicians have to use intubation procedures to establish an artificial airway. During these intubation procedures laryngoscopes are used by physicians as an instrument to keep the tongue out of way in order to visualize the epiglottis, so that an endotracheal tube can be inserted into the trachea.

The problem is that all the laryngoscope blades on the market now are narrow and can hold only approximately half of the tongue, so that it is very hard to make the tongue stay on the laryngoscope blade with any degree of stability. The epiglottis is very difficult to visualize and the endotracheal tube is very hard to be insert into the trachea.

If the patient has a cardiac or respiratory arrest, the critical period is four minutes, and quite often the tube can not be placed into the trachea within that critical time period. Consequently, the patient will have needlessly suffered from irreversible brain damage.

My new invention can overcome the above mentioned drawback of intubation. The sheath of this invention contains an aperture through which the common standard laryngoscope blade can be inserted. The sheath contains three means for keeping the tongue stable, the shape is curved, wide, and rigid, so that it can hold the whole tongue stably without slippage.

2. DESCRIPTION OF THE PRIOR ART

Many prior art devices have been used for attachment to a laryngoscope for intubation purposes. The most pertinent prior art is John A Jephcott who discloses a disposable cover (U.S. Pat. No. 3,426,749. (Issued Feb. 11, 1969.)

SUMMARY OF THE INVENTION

There are no known devices that disclose sufficiently rigid and self supporting and significantly wide covers or sheaths to hold the whole tongue and which are curved properly to keep the tongue stable. The sheath should be least rigid enough to be self supporting and support the weight of the tongue. Preferably the sheath will support all the force the tongue muscles can exert. The sheath contains orifices which enhance the visualization of the epiglottis, and a guide groove which directs the endotracheal tube to be easily inserted into the trachea. This is a feature not believed present in the prior art. The guide groove on the underneath surface accommodates the endotracheal tube so it will be supported and can be inserted quickly, easily, smoothly without difficulty. Because this sheath is sterile, disposable and for a single use it can prevent cross infection arising from reuse between patients.

It is an object of the present invention to overcome drawbacks of the intubation process of the prior art. (1) It is an object of the present invention to provide a sheath useable over most laryngoscope blades. (2) A still further object of this invention is provide a sheath that is self-supporting and of a width sufficient to support the tongue in its entirety. (3) An additional object of this invention is to reduce slippage in that the sheath is curved to support the tongue. (4) A still further object of this invention is to enhance the visualization of the trachea by having an orifice on either side of the bottom of the sheath. The light of the laryngoscope can clearly shine through one or the other or both of the sides. (5) The present invention also has the additional object of providing the most sterile environment for the intubation process possible. The sterile sheath coves all parts of the blade so that the blade can be kept from contacting any part of the mouth. After a single use, the laryngoscope blade sheath is disposed of, to prevent cross infection. (6) It is also an object of this invention to reduce cost and enhance the ease of endotracheal intubation by making the sheath from a relatively rigid plastic. (7) It is a further object of this invention to facilitate the intubation process by providing a sheath that will function as one unit with the laryngoscope blade, this improves over the prior art by containing an endotracheal guide groove on its dorsal side so that the sheath unites the instrument involved in this process into one functional unit.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

DETAILED DESCRIPTION OF PERFERRED EMBODIMENT

Figure 1:
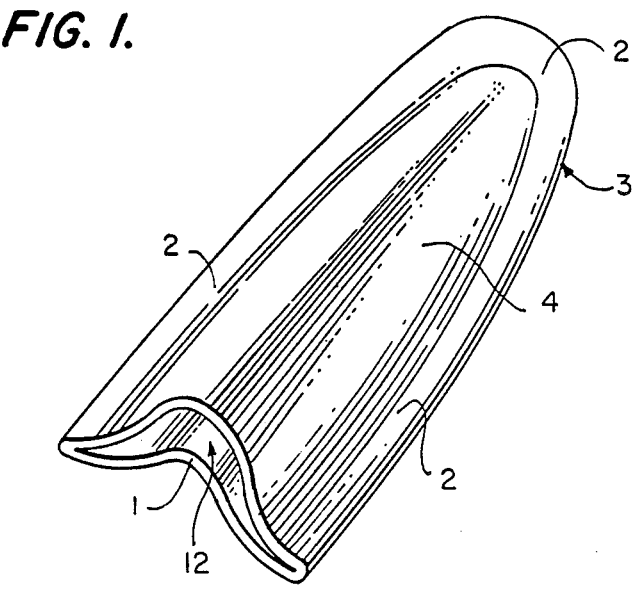
FIG. 1 is an oblique projection of the top plane view and front plane view of an embodiment of the invention.

Referring first to FIG. 1, which shows an oblique projection of the top plane view of the sterile disposable laryngoscope blade sheath, it will be seen that the sheath contains an aperture 1, and channel 12 through which most standard laryngoscope blades will fit. The curved edge 2, which forms a rim, will help to hold the tongue stable during the intubation process. The lateral edge portion 3 will be made sufficiently wide so that the whole tongue may be lifted during the intubation process. The upper face of the strip 4 will give greater support to the tongue.

It should be clearly understood that the particular form of laryngoscope blade illustrated in the drawings is only one example of a considerable number of differently shaped blades which are commonly available for use in various different circumstances, and that the present invention extends to the provision of disposable cover for all forms of laryngoscope blades and not to that which is illustrated.

Figure 2:
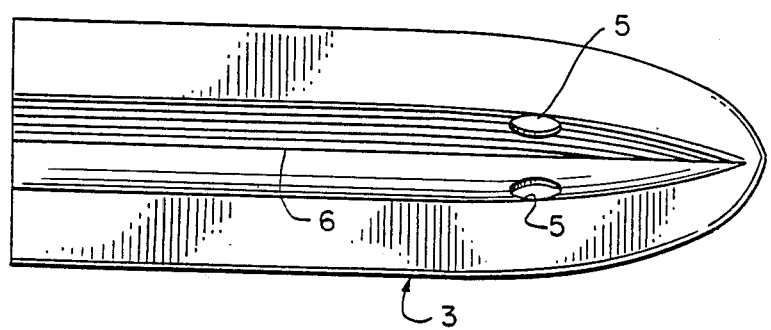
FIG. 2 is a bottom view of an embodiment of the invention.

Referring now to FIG. 2, the sterile disposable laryngoscope blade sheath is shown in a dorsal view. The orifices 5 are shown through which light from the laryngoscope's light source will be directed to visualize the larynzx as well as the intubation guide groove 6 which facilitates the passage of the endotracheal tube 11. By having the dual orifices 5 on either side of the sheath there is increased visualization of the larynx. In addition one can overcome the problem that some laryngoscope blades have their bulb on the right side while others on the left.

Figure 3:
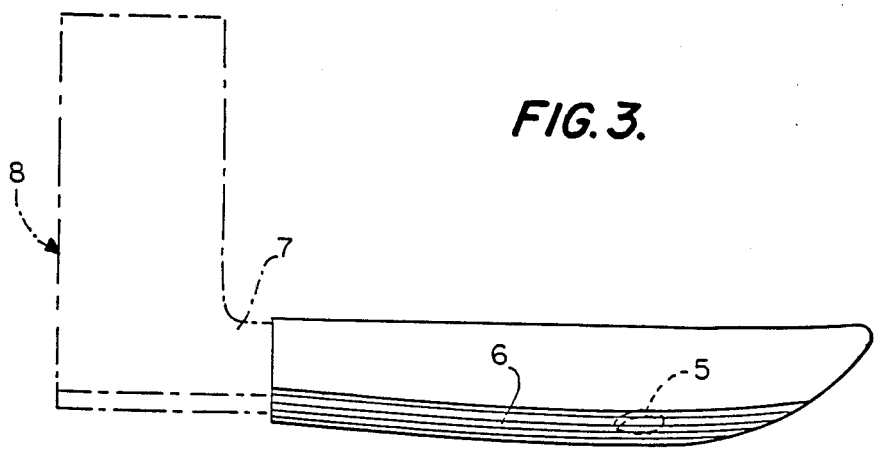
FIG. 3 is a side plane view and perspective illustration of a laryngoscope blade inserted in the present sheath.

Referring next to FIG. 3, there is shown a lateral view of laryngoscope and sterile disposable laryngoscope blade sheath as it would be connected before a typical use in endotracheal intubation. The laryngoscope blade 7 on handle 8 is smaller than the sheath so that any standard laryngoscope blade can be used in connection with the present invention.

Figure 4:
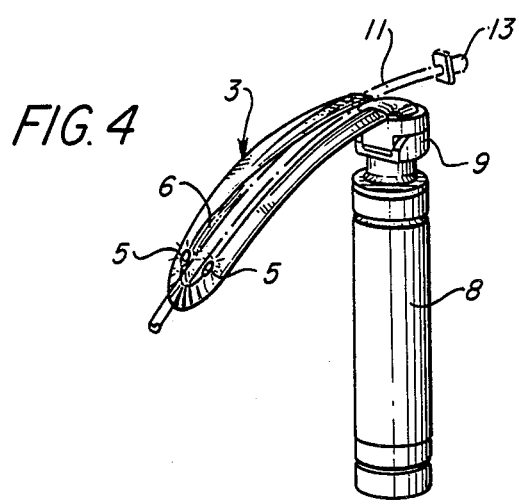
FIG. 4 is a bottom plane view of the present invented sheath with an endotracheal tube in the guide groove on the underneath surface of the sheath and with a standard laryngoscope with its blade connected to the handle and the blade inserted into the aperture of the sheath.

Referring now to FIG. 4, there is shown a bottom plane view of the present sterile disposable laryngoscope blade sheath. It will be seen that the standard laryngoscope is in the sheath with the endotracheal tube in place ready for use in the intubation process. It will be seen that the laryngoscope comprises a handle 8 and a curved stainless steel blade 7 extending substantially at right angles to the handle. The blade is detachably secured to the handle by a claw-type fitting 9. The endotracheal tube 11 is used to maintain an airway for the patient. The endotracheal tube tip 13 will enable the practitioner to connect a respirator to the patient in the event of an emergency.

Figure 5:
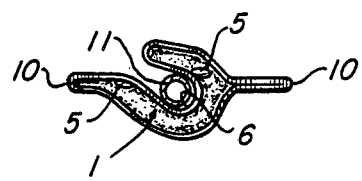
FIG. 5 is a transverse cross section with endotracheal tube in place.

Referring next to FIG. 5, a transverse cross section with the endotracheal tube in place is shown. The sheath 3 has an aperture 1 and orifices 5 formed with intubation guide groove 6 to facilitate the passage of the endotracheal tube 11. The wings 10 are shaped concave and act as abutments to gain greater stability.

Figure 6:
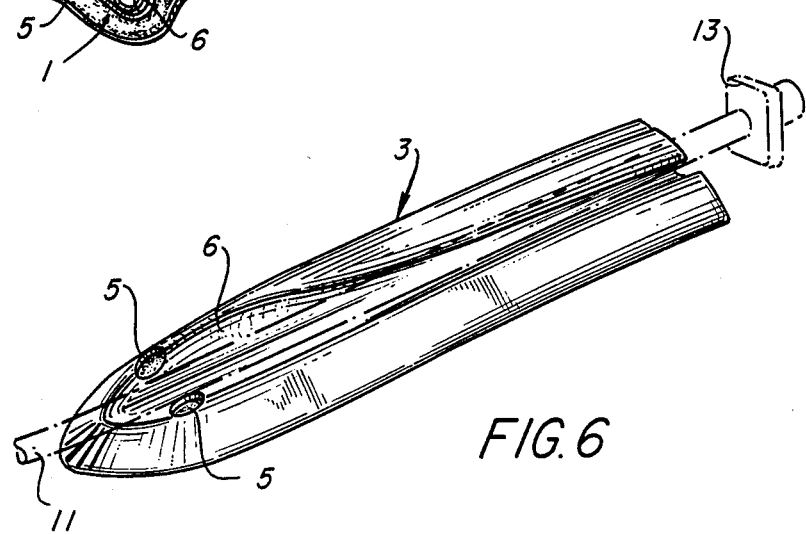
FIG. 6 is a near bottom plane view with an endotracheal tube in place.

Referring now to FIG. 6, there is shown a near bottom plane view with an endotracheal tube 11 in place. The endotracheal tube 11 with the tip 13 are laying on the guide groove 6 between the lateral orifices 5 and lateral edges 3.

The sterile disposable laryngoscope blade sheath will be embodied in a material which is rigid. The higher degree of rigidity of this invention sheath makes it a self-supporting unit.

The standard laryngoscope blades are usually smaller than the sterile disposable laryngoscope blade sheath of the invention. The prior art devices could only uplift half of the tongue while the invention can lift the whole tongue between the lateral edge portion 3 and the upper face of the strip 4. There is a curved edge forming a rim so that the whole tongue not only can be upliftted but also will not slip.

The groove 6 at the bottom of the sheath is a departure from prior art in that the guide groove stablizes the endotracheal tube. The endotracheal tube 11 can be inserted easily directly into the larynx. The light of the laryngoscope blade will project through one or both of the orifices 5 so that the larynx can be visualized clearly and the intubation process can be carried out smoothly and easily.

I claim:

1. A sterile disposable linguiform sheath for mounting on a laryngoscope blade, said sheath containing a longitudinal channel with an orifice for the insertion of a laryngoscope blade, said sheath being formed in such a shape and extending beyond the blade channel a distance sufficient to self support the tongue, said sheath being made from a rigid material such that it is self-supporting and capable of maintaining its shape against the weight of and force exerted by the tongue so as to support the tongue without slippage during use.

2. A sterile disposable linguiform sheath for a laryngoscope blade as defined in claim 1 wherein said sheath is of a size and shape so that it will fit easily into the mouth of infants, children or adults.

3. A sterile disposable linguiform sheath for a laryngoscope blade as defined in claim 1 wherein the bottom of the sheath contains at least one orifice so that a light of the common type can be projected or diffused through it and the trachea can be easily visualized.

4. A sterile disposable linguiform sheath for a laryngoscope blade as defined in claim 1 wherein the edges of the side of the top surface are curved to promote rigidity and support.

5. A sterile disposable linguiform sheath for a laryngoscope blade as defined in claim 1 wherein said sheath is formed to house every portion of the laryngoscope blade inserted into the mouth thus keeping the blade from direct contact with the patient's mouth and reducing the risk of contamination.

6. A sterile disposable linguiform sheath for a laryngoscope blade as defined in claim 1 containing in addition an intubation guide groove to facilitate the introduction of the endotracheal tube and to reinforce the sheath for supporting the tongue and for further stabilizing the intubation process.

7. A sterile disposable linguiform sheath for a laryngoscope blade with a guide groove for instrument guide and support as in claim 6 wherein the sheath is sterilized and is used only once minimizing cross infection.

8. A sterile disposable linguiform sheath for a laryngoscope blade with guide groove for instrument guide and support as in claim 6 wherein said sheath, a laryngoscope and an endotracheal tube are combined to form one self supported synergistic unit making the intubation process more effective and relatively free of difficulties.

9. A sterile disposable linguiform sheath for a laryngoscope blade, said sheath containing a longitudinal channel with an orifice for the insertion of a laryngoscope blade, said sheath being made from a rigid material and being formed in such a shape and extending beyond the blade channel a distance sufficient to self-support the tongue such that it is self-supporting and capable of maintaining its shape against pressures such as that exerted by the weight of the tongue and forces exerted by it, a rigid intubation guide groove formed in said sheath beyond and adjacent to said longitudinal channel and forming a part of the sheath, said guide groove shaped to facilitate the introduction of an endotracheal tube and to reinforce the remaining portion of the sheath and for further stabilizing the intubation process.

10. A sterile disposable linguiform sheath for a laryngoscope blade as set forth in claim 9 wherein the sheath has curved surfaces to hold the tongue motionless during the intubation process.

11. A sterile disposable linguiform sheath for a laryngoscope blade as set forth in claim 10 wherein the sheath additionally contains at least one orifice for use with a light means.

* * * * *